(12) United States Patent
Dickman

(10) Patent No.: US 7,066,960 B1
(45) Date of Patent: Jun. 27, 2006

(54) INTERVERTEBRAL DISK REPLACEMENT

(76) Inventor: Curtis A. Dickman, 2910 N. Third Ave., Phoenix, AZ (US) 85013

( * ) Notice: Subject to any disclaimer, the term of this patent is extended or adjusted under 35 U.S.C. 154(b) by 115 days.

(21) Appl. No.: 10/185,738

(22) Filed: Jun. 28, 2002

(51) Int. Cl.
*A61F 2/44* (2006.01)

(52) U.S. Cl. .................. 623/17.16; 623/13.11
(58) Field of Classification Search ............. 623/17.12, 623/17.16, 23.5, 23.52
See application file for complete search history.

(56) References Cited

U.S. PATENT DOCUMENTS 5,314,478 A * 5/1994 Oka et al. ................. 623/14.12

FOREIGN PATENT DOCUMENTS

| GB | WO 96/01598 | * | 1/1996 |
| GB | WO 98/40111 | * | 9/1998 |

* cited by examiner

Primary Examiner—Thomas Barrett (57) ABSTRACT

An intervertebral disk prosthesis in a preferred embodiment has a matrix of bioincorporable fabric, and a nuclear core centrally mixed into the matrix. The core is formed by impregnating the fabric substrate centrally with a polymer, preferably of liquid form that cures into a viscoelastic solid, in which each component—polymer and fabric—reinforces the other against tearing, shearing and weakening under stress. The core is a hybrid composite adapted for elastic deformation centrally of the matrix, in which the polymer is mixed with the fabric, and is surrounded by the outer bioincorporable fabric margin of the matrix. In another embodiment, the nuclear core is separated from an outer sheath of the bioincorporable fabric by an intermediate ligament encasement that surrounds the purely polymeric core In either embodiment, each edge of the outer fabric that interfaces a vertebral end plate is impregnated with an agent to stimulate osseus incorporation and anchoring. An adjunct anchoring system with penetration of bone of adjacent vertebra may be used to for attachment until and after bioincorporation occurs.

4 Claims, 5 Drawing Sheets

INTERVERTEBRAL DISK REPLACEMENT

BACKGROUND OF THE INVENTION

The present invention relates generally to intervertebral disk prostheses, and more particularly to improvements in and anchoring systems for disk prostheses to assure operation, fixation and stabilization of the prosthesis corresponding to a natural disk.

The human backbone (the vertebral or spinal column) 10 (FIG. 1) consists of numerous longitudinally aligned vertebrae 11, adjacent ones of which are separated by individual cartilaginous intervertebral disks 12 and connected to one another by ligaments. The vertebral column is the vertical axis of the skeleton, extending from the skull (not show) at its proximal end to the pelvis (not shown) at the distal end. It serves to support the head and trunk of the body, and to protect the spinal cord (not shown) that passes through the vertebral (spinal) canal formed by openings in the vertebrae. Adjacent the distal end of the vertebral column, the sacrum portion 13 of the pelvis is formed by several vertebrae that are fused together and to which the coccyx (tailbone) 14 is attached.

The flexibility of the overall vertebral column allows movements of the trunk in flexion or bending forward, lateral flexion or bending sideways, extension or bending backward, rotation about its longitudinal axis, and circumduction, which is a combination of the aforementioned movements. However, these movements are attributable to the cumulative effect of the numerous small movements that take place at the joints between the vertebrae.

Figure 1:
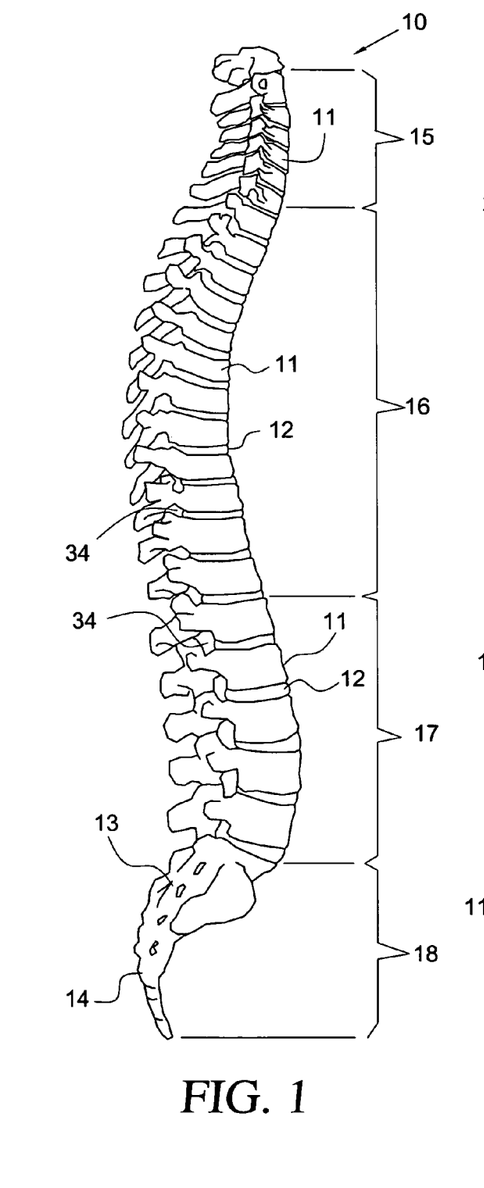
FIG. 1 is a lateral side view of a human vertebral column.

As shown in FIG. 1, the vertebral column 10 has an upper cervical curvature 15, a middle thoracic curvature 16, a lower lumbar curvature 17, and a lowest pelvic curvature 18. The cervical region comprises seven vertebrae, the thoracic region twelve vertebrae, and the lumbar region five vertebrae (for convenience, all of the vertebrae are depicted by reference number 11), with various common characteristics as well some different features according to the functions the respective vertebrae serve. For example, the first cervical vertebrae is configured to support and balance the head, and the second is configured to pivot within the first as the head is turned from side to side, respectively. These vertebrae are atypical, possessing certain structural features not found in the others. The thoracic vertebrae have larger bodies than the cervical vertebrae to accommodate increased stress as a result of their support of successively increasing body weight, and the lumbar vertebrae still larger bodies for the same reason.

Figure 2:
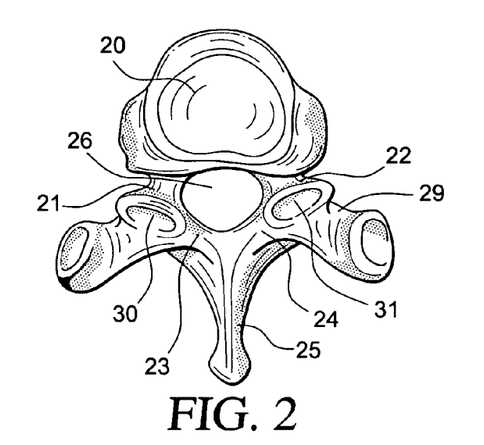
FIG. 2 is a top view of a typical vertebra in the vertebral column of FIG. 1.

A typical vertebra 11 is depicted from above in FIG. 2, which illustrates the bony vertebral body 20 anteriorly of the intervertebral column 10, aligned along the respective curvatures with the bodies of the other vertebrae of the column. A bony vertebral arch is formed by a pair of posteriorly projecting pedicles 21, 22, and laminae 23, 24 extending from the pedicles and joined together as the spinous process 25, the arch surrounding a vertebral foramen 26 aligned with corresponding foramen of the other vertebrae to form a vertebral or spinal canal for passage of the spinal cord (not shown). Transverse processes 28, 29 project from between the pedicle 21 and the lamina 23 on one side, and 22 and 23 on the other, respectively. Superior 30, 31 and inferior (hidden from view in FIG. 2) articular processes have cartilage covered facets for joining adjacent vertebrae above and below to the vertebra shown in FIG. 2. Notches on the lower portion of the pedicles 21, 22 create intervertebral foramina openings (34, FIG. 1) through which spinal nerves (not shown) pass between adjacent vertebrae to connect to the spinal cord.

The facet joints on each side between the articular processes of adjacent vertebrae constitute two of the three separate intervertebral joints between each vertebra and the adjacent vertebra above (or below) it. The third is the anterior joint formed between the bodies of adjacent vertebrae by the intervertebral disk 12 which both unites them and allows movement between them. The type and degree of movement of the vertebral column acting as a unit is controlled by the actions of all three intervertebral joints between the separate vertebrae, allowing, for example, pure rotation of the column only in the thoracic region.

The intervertebral disks 12 separating the vertebrae are masses of fibrocartilage that cushion and soften forces arising from movements such as walking and jumping, as well as providing one of the joints between the adjacent vertebrae. The disks are shaped according to their locations in the spine. Those in the thoracic region are relatively thinner and flatter than the disks in each of the cervical and lumbar regions, which are wedge-shaped and relatively thicker. Anterior and posterior longitudinal bands of ligamentous fibers extending along the length of the vertebral column and attached to the bodies of the vertebrae serve in part to reinforce the disks in front and behind.

Each disk 12 itself is composed of a tough outer layer of the fibrocartilage and an elastic central region. Injury, exertion or the aging process can produce changes in the disks, such as loss of firmness of the central region and thinning, weakening and cracking of the outer layer as a result of degenerative changes, and breakage of the outer layer and squeezing out of the central region as a result of injury from external pressure or heavy lifting. Pressure on the spinal cord or individual nerves branching from the cord caused by the ruptured or slipped disk often produces back pain, numbness and loss of muscular function in the body parts innervated by the affected spinal nerve(s).

More specifically, each disk has an annulus composed of concentric rings of strong fibers (the annulus fibrosus, or annulus) that surrounds a central gelatinous nucleus (the nucleus pulposus, or nucleus). The annulus fibers are attached in an oblique direction at top and bottom of the disk to the adjacent vertebrae so that some of the fibers tighten when the related vertebrae are rotated in one direction and the others tighten when the rotation is in the opposite direction, to resist torsional motion between vertebral segments and excessive movement in almost any direction. Also, the fibers in adjacent rings are oriented at right angles to enable strong bonding while allowing some movement between the bones. The nucleus is not centered in the disk but resides more toward the posterior, with the annulus thinner in that sector and thicker at the anterior sector. The nucleus is designed for deformation in response to exertion of pressure on the disk so that the disk can change shape during movement of the vertebral column. This accommodates bending of the vertebral column and resulting displacement of confronting surfaces of the adjacent vertebrae from a substantially parallel orientation. In concert, the annulus undergoes stretching in the sector of wider displacement and bulging in the sector of narrower displacement of those opposing surfaces.

Vertebral end plates at opposite ends of the disk abut against the bodies of the respective adjacent vertebrae above and below, operating as a transition zone between the bony vertebrae and the soft intervertebral disk. The disk itself is without blood vessels, so it receives its nutrients for metabolism by diffusion through the end plates.

The intervertebral disk can become herniated when the fibers of the annulus weaken or tear as a result of abnormal or repeated stress or because of degenerative processes with aging. The nucleus then tends to become distended and unable to recover to its normal position within the annulus. In such cases, nerve compression can occur as the bulging disk penetrates the vertebral canal and begins exerting ongoing pressure on the spinal cord or on individual nerves that pass between adjacent vertebrae and connect to the spinal cord. This occurs most often with disks located in the lumbar region, where the greatest stresses attributable to weight are present. The result is chronic lower back or leg pain, which can be disabling.

A common procedure in such cases, typically after first having attempted a conservative approach with treatment regimens of anti-inflammatory drugs, patient rest, or physical therapy or a combination thereof, without significant success, is to surgically remove the defective disk, implant patient or donor bone, and/or fuse the adjacent vertebrae, so as to alleviate the pain at least to an extent.

While fusion enjoys success in alleviating symptoms and stabilizing the joint at the previous vertebra-disk interface, it decreases the range of motion of the vertebral column in the portion of the region where the surgical procedure was performed. Also, the biomechanical rigidity of the fused vertebrae may exacerbate deterioration of adjacent portions of the region.

Artificial intervertebral disks or disk prostheses offer replacement of the defective natural intervertebral disk with a capability of performing many of the functions of the latter, at least to an extent to reduce problems suffered as a result of the defects, and an opportunity to avoid further degeneration of the vertebral column.

Artificial intervertebral disks, partial disk prostheses and techniques of fixation thereof have been proposed in several United States patents, including the following.

U.S. Pat. No. 3,867,728 discloses a synthetic kidney shaped prosthetic disk with a core (nucleus) composed of biocompatible viscoelastic liquid or elastomer contained in a sealed chamber such that the core resists deformation under compressive loading. The walls of the chamber are surrounded by medical elastomer layers reinforced with embedded fibrous material such as Dacron filaments. The fibrous material is intended to act as an open-pore, tissue ingrowth-receptive surface that abuts the exposed bony surface of an adjacent vertebra when resident between the natural surfaces of the vertebral cavity from which the replaced disc was excised. The elastomeric core is reinforced with an annular ring of laminated fibrous material embedded in the elastomer. The biocompatible viscoelastic liquid core has reinforced side and end walls of medical grade elastomer with embedded fibrous material to provide a sealed chamber for the liquid, and an open pore tissue-ingrowth receptive surface positioned to abut the exposed bony surface of an adjacent vertebra.

U.S. Pat. No. 4,772,287 discloses a prosthetic disc capsule for repairing a natural herniated disk. The prosthesis has an outer layer composed of strong inert fibers that surrounds a bladder containing a thixotropic gel having a viscosity and velocity shear behavior imitating that of a natural spinal disc. One or more of the capsules are inserted into bores formed in the natural herniated disc under repair. The inert fibers of the outer layer are composed of carbon or a polymer, including either natural or synthetic polymers such as cold-drawn poly(ethylene terephthalate) polyester fibers, or of bioresorbable material consisting of polylactic or polyglycolic acid or collagen (e.g., semi-synthetic), for replacement by tissue ingrowth for bonding to surrounding tissue. The bladder is flexible, composed of oriented poly (ethylene terephthalate), high-density polypropylene, silicone rubber, and copolymers of silicone and carbonate. The thixotropic gel is a mixture of an inorganic oil such as silicone or fluorocarbon, and a gelling agent such as fumed silica. The viscosity of the gel is selected to permit fast movement during bending at the intervertebral space while restricting motion during slow postural changes.

U.S. Pat. No. 4,946,378 discloses an artificial intervertebral disc with a pair of metallic end bodies having 0.1 to 0.5 mm hydroxyapatite layer-coated outer surfaces and a biocompatible synthetic elastic polymeric intermediate material of silicone rubber, polyvinyl alcohol, polyurethyane resin, or the like held between the end bodies through connecting members composed of titanium, stainless steel, or the like.

U.S. Pat. No. 5,047,055 discloses a prosthetic lumbar disk nucleus fabricated from synthetic hydrogels selected because of their biocompatibility, characteristics of softness, hydration, low friction, viscoelasticity, shape memory, and mechanical strength which can aid the healing of a defective annulus of the intervertebral disk. The prosthetic nucleus may purportedly be implanted in the dehydrated state laterally to reduce the complexity and risk of traditional intraspinal surgery, and allowed to swell slowly in the body thereafter, with reduced incision area on the annulus to aid healing of the annulus and prevent herniation of the disk. The implanted hydrogel nucleus, after hydration, is constrained tightly in the cavity formed by the excised natural nucleus, by the restoring force of stretched fibers of the annulus and the external force through the end plates.

U.S. Pat. No. 5,192,326, a continuation-in-part of the '055 patent, also discloses a prosthetic lumbar disk nucleus, but in which the nucleus is composed of hydrogel beads.

U.S. Pat. No. 5,258,043 discloses a prosthetic disk is composed of a dry, porous, volume matrix of biocompatible and bioresorbable fibers, a portion of which may be cross-linked, structured for implantation to assume the form and role of a natural intervertebral disk. The matrix may promote regrowth of intervertebral fibrochondrocytes and provides a scaffold for the regenerating intervertebral disk tissue. The prosthetic disc may further include a mesh composed of a bioresorbable, biocompatible material attached to lateral portions of the outer surface of the matrix to aid disk implantation by providing a temporary anchoring mechanism.

U.S. Pat. No. 5,458,643 discloses a prosthesis in the form of an artificial intervertebral disk composed of polyvinyl alcohol (PVA) hydrogel and a porous ceramic or metal. The PVA hydrogel is said to enhance lubrication and shock absorbing functions, and the porous body to allow the ingrowth and ossification of adjacent bone tissue of the body in which the prosthesis is implanted.

U.S. Pat. No. 5,824,093, related to the '287 patent cited above, discloses a prosthetic disk capsule to be implanted in pairs side-by-side in a damaged natural intervertebral disk to maintain both height and motion. Each capsule is an elongated, prosthetic spinal disc nucleus body composed of a hydrogel core and a surrounding constraining jacket that permits the hydrogel core to deform and reform and to hydrate to a predetermined volume with deformation and reformation in response to various loads placed upon the spinal tract.

At least some of these artificial intervertebral disks present the possibility of successful implants on a practical scale. However, so far as is known to the applicant herein, the prior art has not given promise of successful implementations and methods for anchoring implanted artificial intervertebral disks in the vertebral column to achieve relatively permanent fixation and stabilization of the implant.

U.S. Pat. No. 5,562,738 discloses an intervertebral disk arthroplasty device for replacing a degenerated or ruptured intervertebral disk. The disk includes a first member with a socket portion and a second member with a ball portion fitting in the socket portion. The first member fits adjacent the first vertebrae and the second member fits adjacent the second vertebrae so that the ball portion fits in the socket portion, in the space vacated by the excised disk. The members are anchored in place by base plates with tabs fastened to the members, and by screws through the tabs into the adjacent vertebrae. A second embodiment utilizes metal insert cups fastened to the members, and another embodiment contemplates bone ingrowth into ceramic members.

Prior art artificial intervertebral disks, and techniques of fastening, anchoring and stabilizing implanted artificial disks do not appear likely to yield satisfactory results.

It is a primary aim of the present invention to provide improved intervertebral disk prostheses, and anchoring systems that achieve reliable stabilization and relatively permanent fixation of the improved intervertebral disk prosthesis in a vertebral column.

Another aim of the invention is to provide methods of fabricating intervertebral disk prostheses, and of anchoring the prosthesis, for achieving those results.

SUMMARY OF THE INVENTION

In essence, the intervertebral disk is an anatomical spacer, stabilizer, load dampener and shock absorber, positioned between the vertebral end plates. The disk and surrounding ligaments also stabilize the spine, connect adjacent vertebrae, and prevent excessive rotation and subluxation of the vertebrae. As noted in the background section above, intervertebral disks have some desirable deformability attributable to their viscoelastic properties. They also demonstrate hysteresis, and have a high degree of hydration. The hysteresis is exhibited in response to the mild deformability of the disk under compressive loading, when, after unloading, the disk rebounds to its normal position. This resiliency to compressive loading and unloading is a key function of the disk. To yield suitable results, an artificial disk—a disk prosthesis—must replicate all of these properties, characteristics or functions of the natural intervertebral disk.

According to an important aspect of the invention, a disk prosthesis is fabricated in a unified structure comprising a matrix or substrate of bioincorporable continuous fabric and a nuclear core or nucleus that is centrally impregnated into the substrate and retained in place therein without a separate surrounding sheath. Preferably, the substrate is woven collagen fabric, and the nucleus is a hydrogel polymer centrally impregnated by injection or soaking into the continuous substrate. The collagen fabric is woven for tensile strength. The polymer is preferably an injectable, curable liquid that, upon setting, forms a viscoelastic solid in which each component reinforces the other. This makes it less likely that the fabric component or the polymeric component will tear, shear or weaken under stress; after the prosthesis is implanted into a vertebral column and subjected to the normal forces associated with spinal movements. Instead of a viscoelastic solid, the polymer may be retained in a liquid or semi-liquid state that impregnates the fabric at the core. In any event, the nuclear core is a hybrid composite of the two primary materials. Outside the core, the substrate defines an outer bioincorporable fabric margin. The overall prosthesis is a deformable solid adapted for elastic deformation as a result of its structure.

The intervertebral disk prosthesis of the invention possesses characteristics of being compressible, mildly deformable, resilient, hydrated, durable, nontoxic, nondegradable, nonfragmenting, and viscoelastic, among other properties. The prosthesis acts as a solid material to provide structural spacing and load dampening effect between vertebral end plates. It is suitable for replacement of a damaged natural disk in any of the cervical, thoracic or lumber spinal regions of the vertebral column.

In an alternative embodiment, the nuclear core is a separate viscoelastic region surrounded by fabric encasement, centrally of an outer bioincorporable fabric sheath.

It is equally important that an artificial intervertebral disk, when implanted, be suitably and reliably anchored in place, again mimicking the anchoring of a natural disk in the vertebral column. The anchoring systems of the present invention target bone ingrowth into the outer fabric margin or sheath of the disk prosthesis as the primary mechanism or biomechanism for attachment of the prosthesis, with subordinate or adjunct assistance of other fasteners where appropriate. To that end, the outer edge of the fabric matrix is impregnated or surface coated, at least at the sides where the disk interfaces the vertebral end plates, with one or more biological agents that promote growth and incorporation of bone, fibrocartilage or fibrous tissue into the fabric, for osseus incorporation and anchoring, to provide both near and long-term post-implantation stability. Suitable agents include growth factors, hydroxyapatite and BMP, for example.

A total or integrated anchoring system according to the invention may comprise one or more anchorage mechanisms, at least one of which is the above-stated bioincorporation of the disk prosthesis structure to adjacent vertebrae. Adjunct anchoring mechanisms may comprise mechanical and/or biological fasteners such as titanium screws, bioincorporable cement, natural ligaments or artificial ligamentous members, or platforms, may be used to provide immediate stability of the implanted disk prosthesis until osseus incorporation occurs. The immediate stability system may use resorbable or nonresorbable materials for permanent reinforcement of the anchorage.

BRIEF DESCRIPTION OF THE DRAWINGS

The above and still further aims, objectives, features, aspects and attendant advantages of the present invention will become apparent from the following detailed description of a preferred embodiment of the interventional device and method of use thereof, constituting the best mode presently contemplated of practicing the invention, when taken in conjunction with the accompanying drawings, in which.

DESCRIPTION OF THE PRESENTLY CONTEMPLATED BEST MODE OF PRACTICING THE INVENTION

Figure 3:
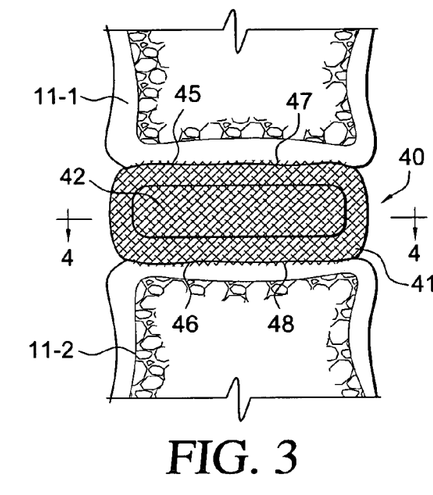
FIG. 3 is a simplified anterior side view of an embodiment of an intervertebral disk prosthesis according to the invention, positioned between adjacent vertebrae.
Figure 4:
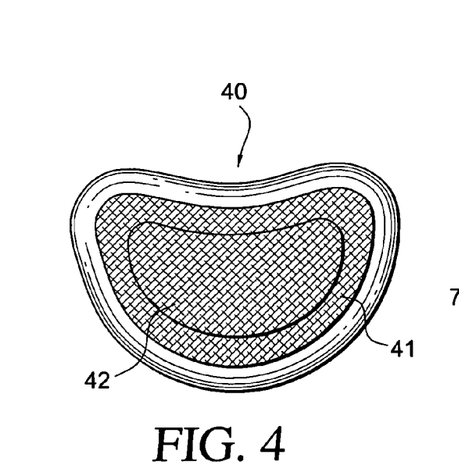
FIG. 4 is an axial cross-section view of the disk prosthesis embodiment of FIG. 3, taken along the lines 4—4.

Referring to FIGS. 3 and 4, a presently preferred embodiment is a unified composite disk prosthesis 40, shown as being positioned following implantation between the bodies of two vertebrae 11-1 and 11-2 of the vertebral column, as viewed anteriorly (FIG. 3). Prosthesis 40 includes a matrix 41 with a substrate of bioincorporable continuous fabric. In its central region, the substrate is impregnated with a liquid or semi-liquid polymer—preferably a hydrogel polymer—that intermixes with the substrate fabric in that region to form a nuclear core (nucleus) 42. This core is a hybrid composite of the two materials, a central mix of polymer and fabric that is elastically deformable and accurately mimics the nucleus pulposus of a native or natural disk.

The polymer is preferably an injectable, curable liquid that, after injection into the central region of the substrate, sets to form a viscoelastic solid. Alternatively, the liquid may be soaked into the fabric at the central region of the substrate. In other embodiments, the core may retain the polymer in a liquid or semi-liquid or gelatinous state intermixed with and impregnated into the fabric of the substrate to form the hybrid composite. In either of the latter embodiments, a ligamentous encasement may be used to encompass the core, and the substrate fabric within and outside the core may be separate.

The hybrid composite core constitutes a medium in which each component—polymer and fabric—reinforces the other to deter damage from occurrences such as tearing, shearing or weakening under the types of stress to which the intervertebral disk prosthesis will be subjected as an implant in the vertebral column of a normally active person, even an elderly person.

Outside the core, the substrate fabric is relatively devoid of the polymer, and constitutes a bioincorporable fabric margin that runs to the edge of the disk prosthesis and surrounds the core 42.

The disk prosthesis 40 of the preferred embodiment is relatively solid, but the structure of its matrix and core adapts it to undergo elastic deformation when under compression or subjected to other forces as a result of movement of or along the vertebral column, according to the nature of the movement. The original size and shape of the prosthesis are restored when the pressure attributable to the movement is removed, by virtue of its elastic deformation.

Matrix 41 may be fabric made from bioincorporable continuous woven fibers of collagen, polyethylene, or other biocompatible or bioincorporable ligamentous material. A woven collagen fabric is preferred for its tensile strength. Preferably, the fibers are woven to criss-cross each other in layers.

Viewed from the top as shown in FIG. 4, the typical disk prosthesis 40 has the distinctive kidney shape of the natural disk it is intended to replace. Viewed anteriorly or laterally (FIG. 3), the geometry of the prosthesis is relatively flat and rectangular in the unloaded (relatively uncompressed) state as shown, for replacing a natural disk in the thoracic region 16 of the vertebral column (FIG. 1). In that region, adjacent vertebral end plates are substantially parallel. The geometry of the prosthesis is lordotic with a trapezoidal configuration for disk replacements in the lumbar or cervical regions 17 and 15, respectively, owing to the normal curve of the spine. The fabrication of the intervertebral disk prosthesis of the invention allows it to be used in any of the lumbar, cervical and thoracic regions, subject only to those differences in geometry.

At the ends 45, 46 of disk prosthesis 40 that interface the upper and lower (viewed from the side with the vertebral column in an upright orientation) vertebral end plates, the fabric margin of matrix 41 that surrounds the core 42 is impregnated with one or more biological agents that promote growth and incorporation of bone, fibrocartilage or fibrous tissue into the fabric, for osseus incorporation and anchoring of the disk. Preferably, one or more agents such as growth factors, hydroxyapatite, BMP, or others that will stimulate osseus incorporation into the matrix fabric, to simulate natural ligament insertion in bone, are selected for impregnation of the fabric margin at those surfaces. This ingrowth into the fabric is the primary mechanism targeted by the invention to achieve attachment and stabilization of the disk prosthesis 40 to the adjoining vertebrae, as illustrated at interfaces 47 and 48. It is also possible to apply bioincorporable cement at those interfaces with end plates of the vertebrae 11-1 and 11-2 before the disk prosthesis is inserted into the space vacated by the excised damaged disk.

Also, the nuclear core may be transformed into a biologically active material by injecting transfected or genetically engineered cells into the core to create fibrocartilage that prompts the transformation.

With the construction of the disk prostheses of the invention, the bone growth mechanism of attachment (anchorage) will provide long-term fixation and stabilization of an implanted prosthesis. Such anchorage is sufficient for the prosthesis to withstand virtually continual stresses as the patient engages in walking (and perhaps jumping and running as well), bending forward, bending sideways, bending backward, and twisting of the trunk, in normal everyday activity, not necessarily involving strenuous exercise.

Figure 5:
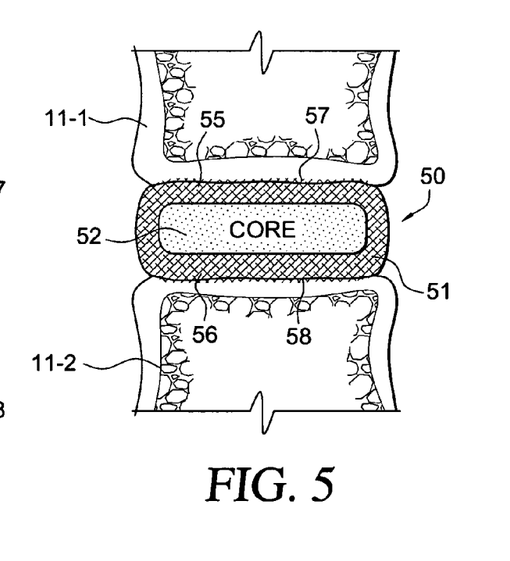
FIG. 5 is a simplified anterior (or lateral) side view, partly in section, of an alternative embodiment of a disk prosthesis.

An alternative embodiment of the disk prosthesis is illustrated, partly in section, in FIG. 5. Prosthesis 50 has an inner nuclear core 52 of viscoelastic solid (or, alternatively, liquid or semi-liquid) polymer, preferably hydrogel or hydrogel composite material. In this embodiment, however, the core is a separate component. In liquid or semi-liquid state, the core may be encapsulated in an intermediate ligamentous encasement 55, such as collagen fabric or other bioincorporable material. An outer bioincorporable continuous fabric sheath 51 surrounds the core, and encompasses the ligamentous encasement if used. The sheath may have the same composition as that of matrix 41 in the preferred embodiment of FIGS. 3 and 4, i.e., bioincorporable continuous woven fibers of collagen, polyethylene, or other biocompatible or bioincorporable ligamentous material.

As with the previous embodiment, disk prosthesis 50 substantially conforms to the shape of a natural intervertebral disk according to whether the prosthesis is a replacement for a damaged natural disk in the cervical, thoracic or lumber spinal region of a human vertebral column.

Here again, to provide the primary anchoring mechanism of ingrowth into the outer fabric of the prosthesis 50, the outer edge (e.g., 56) of the sheath is impregnated or surface-coated with one or more biological agents that stimulate growth and incorporation of bone, fibrocartilage or fibrous tissue into the outer fabric sheath, for osseus incorporation and anchoring, at least at its ends where the prosthesis is to interface with vertebral end plates when implanted. The selected agent(s) preferably include growth factors, hydroxyapatite, BMP, or other agent for osseus incorporation into the outer fabric sheath, to simulate natural ligament insertion in bone The resulting osseus incorporation is illustrated at contact areas 57 and 58.

For some patients, additional fixation and stabilization may be required. For that purpose, and also in instances where it may be desired to provide an immediate attachment until or even after the osseus incorporation occurs, the invention provides adjunct anchoring mechanisms. These may comprise mechanical and/or biological fasteners such as titanium screws, bioincorporable cement, natural ligaments (e.g., cadaveric ligament transplants) or artificial ligamentous members, or platform or plate attachment at the interface areas. Resorbable or nonresorbable materials may be used for permanent reinforcement of the anchorage.

The adjunct anchoring systems of the invention fall into three distinct categories, each of which involves at least some penetration of vertebral bone. One category involves an integration of an anchoring mechanism into the disk prosthesis itself (integrated adjunct anchoring system). A second category involves an anchoring mechanism separate from the disk prosthesis (separate adjunct anchoring system). And the third category involves an anchoring mechanism partially integrated into and partially separate from the disk prosthesis (partially integrated adjunct anchoring system).

In one mechanism, extensions such as of the fabric matrix integral with the disk prosthesis are employed for anchoring. In another aspect, separate adjunct anchoring mechanisms including ligaments fastened or bonded to the adjacent bone serve as tension bands for the vertebrae adjacent to the implant and for confining the disk in place. Additional spinal stability may be provided by fastening to dorsal spinal elements. Another aspect resides in partially integrated adjunct anchoring mechanisms comprising biocompatible metal plates or platforms that affix the disc prosthesis in place with novel configurations that capture the prosthesis through its fabric sheath.

Figure 6:
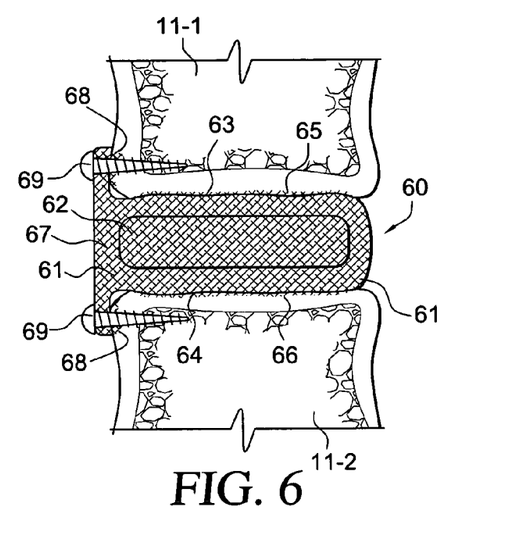
FIG. 6 is a simplified lateral side view, partly in section, of one embodiment of a fully integrated adjunct anchoring system for the prosthesis, according to an aspect of the invention.

One embodiment of an integrated adjunct anchoring system is illustrated in FIG. 6. In this embodiment, the intervertebral disk prosthesis 60 has a nucleus 62 surrounded by a confining matrix or sheath 61 in much the same way as the disk prostheses illustrated in FIGS. 3–5. Here also, matrix 61 is impregnated at its ends 63, 64 with bone growth-promoting elements for rapid incorporation of bone in areas 65, 66 from the surface regions of the adjacent vertebral bodies 11-1, 11-2 between which the disk prosthesis is to be inserted in the implant procedure. But in this embodiment, a ligament or ligamentous member 67 is integrated longitudinally into the disk prosthesis by surrounding the ligament with the matrix 61 along a sector of the side of the prosthesis. The ligamentous member may be a natural ligament, taken from the patient or a donor, or composed of an analog of the natural tissue, or of a synthetic material that preserves its function as a flexible band adapted to connect bones.

The principal criteria for selection of other than natural material are that the ligamentous member must have the tensile strength and biocompatibility of a natural ligament. The ligament need not occupy a very large sector (using either an anterior or lateral approach, with the ligament oriented accordingly) of the disk prosthesis; indeed, it may be a relatively thin strip with dimensions, for example, in a range from about 10 to about 25 mm wide, from about 10 to about 40 mm long, and from about 3 to about 10 mm thick. The matrix 61 is one of the two disk prosthesis embodiments, and thus impregnated with ingrowth agent(s) along its inner surface 68 adapted to contact the surface of the vertebral body 11-1 or 11-2, to promote ingrowth of bone, fibrous tissue or fibrocartilage for anchorage in that area.

The adjunct anchoring mechanism comprising integrated ligament 67 with its surrounding matrix 61 is secured to the anterior or lateral side of the bone of each adjacent vertebrae by a pair of biocompatible screws 69, preferably of titanium, biocompatible alloys or bioresorbable material. The disk prosthesis 60 is there firmly affixed in the vertebral column, with the primary anchorage mechanism providing the capability to respond to forces exerted along the column in substantially the same manner as a natural intervertebral disk. The disk prosthesis is not hindered by the adjunct anchoring mechanism from spreading laterally at the location of that anchoring mechanism. For example, if compressive forces are exerted longitudinally at the anterior of the adjacent vertebrae, the nucleus 62 will tend to compress and spread outwardly in that sector, urging itself against the sheathed ligament 67, which itself has tended to buckle anteriorly under the same compressive forces. When the compressive force is removed, both the nucleus and the sheathed ligament will return to their original size and shape, the sheathed ligament being urged to do so under forces exerted by the restoration of the nucleus from its elastic deformation.

Figure 7:
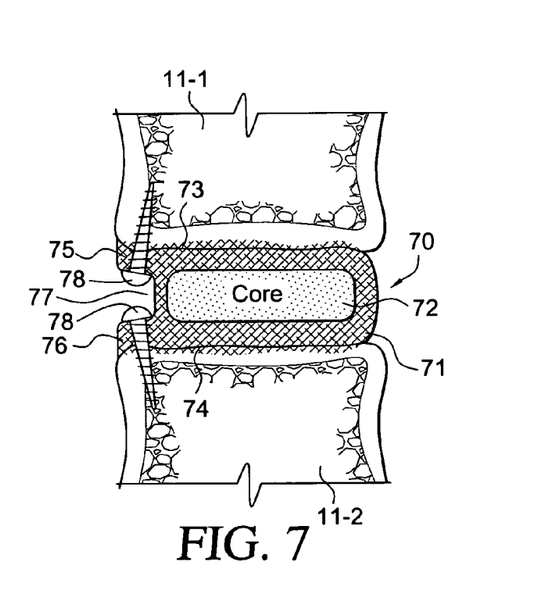
FIG. 7 is a simplified lateral side view, partly in section, of another embodiment of a fully integrated adjunct anchoring system.

Another embodiment of an integrated adjunct anchoring system is illustrated in FIG. 7. Here, the disk prosthesis 70 has a core 72 which is less expansive anteriorly than the confronting or opposing surfaces of the vertebral bodies 11-1 and 11-2 between which it is to be sandwiched on implant. This is to provide the feature of an anchoring mechanism in which the fabric or fibrous sheath 71 extends anteriorly beyond the core at its ends 73, 74. The tabs or projections 75, 76 of the sheath define a channel or opening 77 that allows a pair of biocompatible screws 78 to be threaded into the bone of the respective vertebral bodies 11-1, 11-2 during the implant procedure, thereby securely fastening the disk prosthesis 70 in place in the vertebral column. The channel 77 may be formed by a "scooping out" of the core 72 in that sector, so that the size and shape of the core is only minimally reduced relative to the confronting surfaces of bone. Here also, the sheath 71 is impregnated at its ends 73, 74 with bone growth-promoting elements for relatively rapid incorporation of bone into the prosthesis in the area of the confronting surface regions of the adjacent vertebrae. This embodiment is less preferred than that of FIG. 6 because the core has less opportunity to spread anteriorly under longitudinal compressive force exerted along the anterior of the vertebral column, since the sheath will tend to constrain such movement as the projections 75, 76 are being squeezed together.

Figure 8:
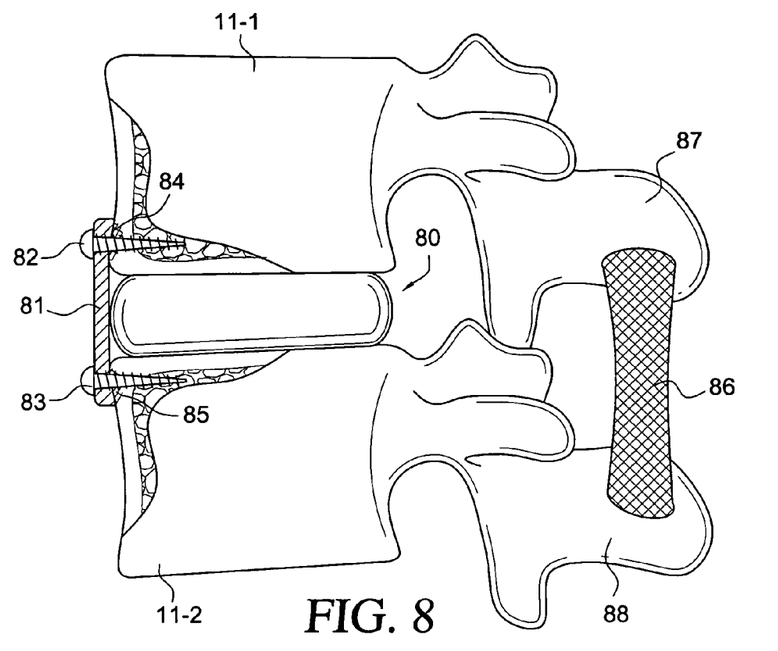
FIG. 8 is a simplified lateral side view of an embodiment of a separate adjunct anchoring system, according to another aspect of the invention.

An embodiment of a separate adjunct anchoring system for a disk prosthesis is illustrated in FIG. 8. The disk prosthesis 80 is implanted between vertebral bodies 11-1 and 11-2 in the space from which the natural disk has been removed. A ligamentous member 81 is implanted and secured as a tension band longitudinally between the vertebral bodies 11-1 and 11-2 by fasteners such as biocompatible screws 82 and 83, respectively, at the anterior or lateral portions of the vertebral column. Again, member 81 may be a natural ligament, or analog or synthetic ligament such as a bioincorporable fabric. Bone ingrowth factors are impregnated in portions 84, 85 of the ligament that are to reside against the vertebral bone to hasten bone incorporation and bonding therewith. The ligament serves not only to maintain the maximum spacing and provide a tension band between the related vertebrae, but to confine the disk prosthesis in place.

The ligament 81 constitutes part of an adjunct anchoring mechanism that is unattached to but in contact with the disk prosthesis.

To add further spinal stability, the adjunct anchoring system may employ a second ligamentous member 86 placed longitudinally on dorsal spinal elements 87, 88 bounding the disk prosthesis 80 at the posterior side of the vertebral column. Ligament 86 may be secured to the dorsal elements by any suitable fastener, such as screws, cables, sutures, wires, or cement, to name a few.

Figure 9:
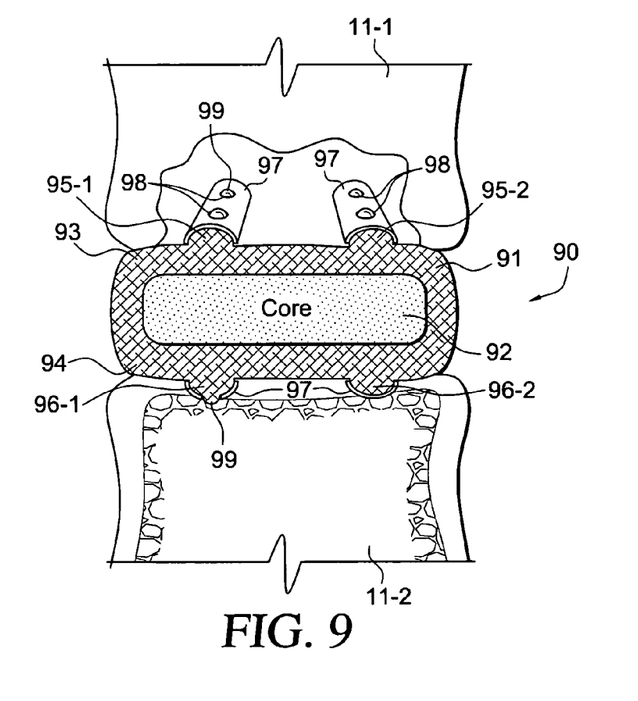
FIG. 9 is a simplified perspective view, partly in section, of an embodiment of a partially integrated adjunct anchoring system, according to yet another aspect of the invention.

An embodiment of a partially integrated adjunct anchoring system for a disk prosthesis is illustrated in FIG. 9, partly in section viewed from the anterior or lateral portion of the vertebral column, depending on desired location. The disk prosthesis 90 includes nucleus 92 encased within fabric sheath 91. The opposite ends 93, 94 of the fabric sheath are formed with two parallel spaced-apart semicircular humps 95-1 and 95-2 extending parallel to the median or midsagittal plane or coronally oriented if inserted laterally, and spanning the prosthesis at end 93, and a corresponding pair of humps 96-1 and 96-2 at end 94. Except for these differences, the nucleus and the fabric sheath may correspond to those of the embodiments of the earlier description herein.

The contour of each end of the sheath 91 is matched by four semicircular elongate anchoring plates 97 designed to mate with respective ones of the humps on the two ends of the sheath. These plates are preferably fabricated of titanium, but other biocompatible, high strength materials may be used as an alternative. Each anchoring plate has a pair of threaded or knurled circular windows or openings 98 to expose marrow and cancellous bone in the adjacent vertebral bodies 11-1, 11-2 between which the disk prosthesis and the anchoring mechanism will be sandwiched after implantation. The openings 98 are intended to accommodate bone ingrowth into the fabric sheath from the exposed marrow/cancellous bone of the adjacent vertebra. Preferably, the sheath 91 has projecting bone, fibrous tissue, fibrocartilage ingrowth agents (e.g., hydroxyapatite, having morphogenetic proteins) fabric bumps 99 that mate with and project through the openings 98, which are passages or through-holes in the respective plates 97, to spur relatively rapid bone ingrowth. Corresponding bone growth-inducing material is impregnated into the fabric at the ends 93, 94 of the sheath in the spaces between the humps and outside the humps that are destined to contact the bony surface of bodies 11-1 and 11-2.

The contours of the ends of the sheath 91 and the need to position the anchoring plates 97 thereon to fit in the vacated space mandate removal of portions of the bone from the opposing surface of the vertebral bodies 11-1, 11-2, to provide similarly contoured surfaces into which the anchoring plates and the underlying prosthesis will nest when the prosthesis with partially integrated anchoring system is implanted, and to expose the marrow/cancellous bone to the fabric at the openings 98.

The presence of the humps and mating semicircular anchoring plates in the embodiment of FIG. 9 offers some further stability in preventing the disk prosthesis from shifting laterally, anteriorly or posteriorly in the acute period that biological incorporation anchoring is taking place.

Figure 10A:
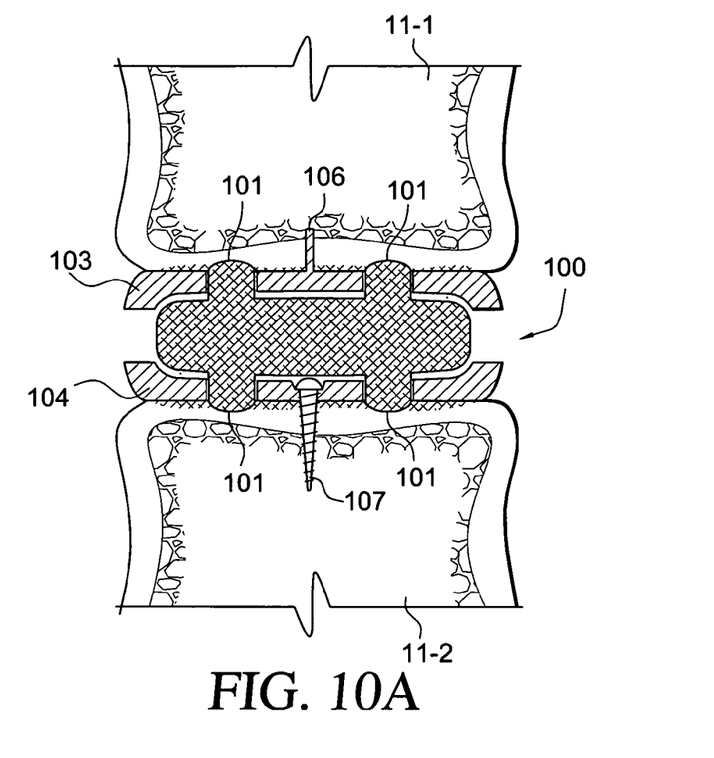
FIGS. 10A and 10B are, respectively, a simplified anterior side view and a top view of a second embodiment of a partially integrated adjunct anchoring system.
Figure 10B:
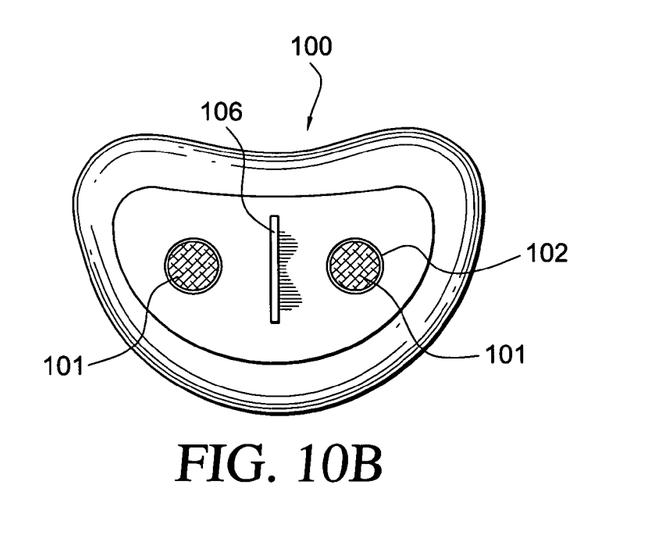

Another embodiment of a partially integrated adjunct anchoring system for a disk prosthesis, that utilizes some of the same concepts present in the embodiment of FIG. 9, is illustrated in FIGS. 10A and 10B. The disk prosthesis 100 comprises a nucleus within a bioincorporable fabric sheath or matrix, as in each of the other embodiments. Here, however, the sheath has a pair of bumps or projections 101 on each of its end surfaces, adapted to align with and enter respective mating through-holes 102 in a pair of plates or platform bases 103, 104 at top and bottom of the disk prosthesis. The plates are adapted, that is, configured and arranged, to confine the prosthesis when implanted along with installation of the anchoring system.

Upper plate 103 has a flat planar projection 106 that spans much of the prosthesis along the median plane, designed to be received within a mating slot (not shown) formed in the bone of the upper vertebral body 11-1. Lower plate 104 is adapted to be fastened to the lower vertebral body 11-2 by one or more screw fasteners 107.

Figure 11:
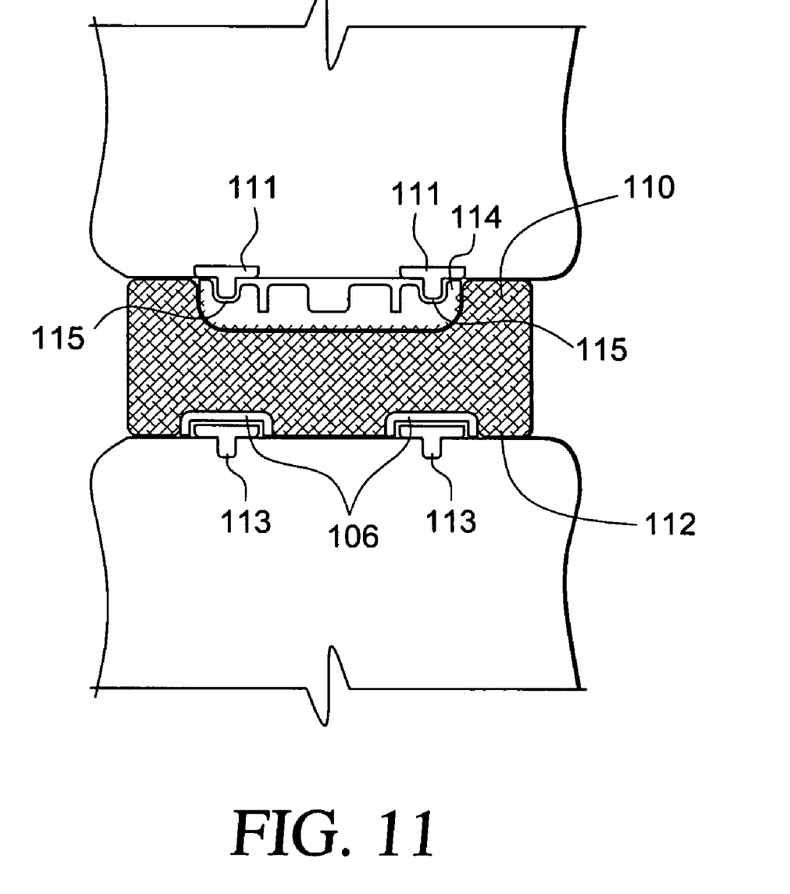
FIG. 11 is a simplified side view of a sliding rail embodiment of a partially integrated adjunct anchoring system.

The partially integrated adjunct anchoring mechanism of FIG. 11 illustrates an embodiment that uses a sliding rail system. In this embodiment, a pair of parallel rails 111 is mounted into one vertebral end plate and another pair of parallel rails 113 is mounted in the adjoining vertebral end plate bounding the space from which the damaged natural disk has been removed. The parallel rails span the end plate on which they are mounted. In this embodiment, each vertebral end plate has the rails oriented perpendicularly in the same direction to prevent improper insertion of the prosthesis. The prosthesis end 110 has an embedded platform 114 with grooves 115 to accept the projecting rails 111. Platform 114 is anchored in the prosthesis with woven fabric of the outer matrix or sheath. The other end 112 of the prosthesis has parallel grooves 116 that match the configuration of the oppositely oriented rails 113, so that the latter are accepted by and slide within the grooves.

In practice, the rails are first mounted into the vertebral end plates, and the prosthesis with its embedded matching configuration of grooves is inserted into the vacant space aligned with the rails, to lock the prosthesis and secure it in position anteriorly, laterally and posteriorly. The primary anchorage mechanism anchors to the bone.

It will be observed that the adjunct anchoring mechanism in each embodiment of the invention is arranged and configured with respect to the disk prosthesis, so that when the prosthesis is implanted and the adjunct anchoring mechanism is installed, there is minimal if any impeding by the anchoring mechanism of elastic deformation of the nucleus of the disk prosthesis under compressive force exerted along the vertebral column.

Although certain preferred embodiments and methods of the invention have been described herein, it will be apparent to those skilled in the art from a consideration of the foregoing disclosure, that variations and modifications of the described embodiments may be made without departing from the spirit and scope of the invention. Accordingly, it is intended that the invention shall be limited only to the extent required by the appended claims and the rules and principles of applicable law.

What is claimed is:

1. An intervertebral disk prosthesis, comprising:
   a bioincorporable fabric matrix having a shape consistent with the shape of the natural disk in a human vertebral column to be replaced by the disk prosthesis; and
   a core region centrally located in said fabric matrix, said core region impregnated with a polymer to form an elastically deformable hybrid composite of the fabric matrix centrally of the disk prosthesis, said core region comprising a cured viscoelastic solid incorporating continuous fibers of the fabric matrix therethrough;
   said fabric matrix extending beyond the boundary of said central core region to form a fabric margin integral with the fabric matrix and surrounding said core region; said fabric margin of the fabric matrix being substantially devoid of said polymer and adapted for attachment and stabilization of the disk prosthesis to adjoining vertebrae in space vacated by the disk being replaced.

2. The intervertebral disk prosthesis of claim 1, wherein said fabric matrix comprises woven collagen for tensile strength.

3. The intervertebral disk prosthesis of claim 1, wherein said fabric margin of the fabric matrix is impregnated with one or more biological agents that promote growth and incorporation of bone, fibrocartilage or fibrous tissue into the fabric margin, for osseus incorporation and anchoring, at least at ends of the disk prosthesis that interface with vertebral end plates when the disk prosthesis is implanted.

4. The intervertebral disk prosthesis of claim 3, wherein said one or more biological agents are selected from a group including growth factors, hydroxyapatite and BMP to simulate natural ligament insertion in bone.

\* \* \* \* \*